(12) United States Patent
Sioli

(10) Patent No.: US 7,109,382 B2
(45) Date of Patent: Sep. 19, 2006

(54) METHOD FOR THE PRODUCTION OF FORMALDEHYDE

(75) Inventor: Giancarlo Sioli, Cernobbio (IT)

(73) Assignee: Casale Chemicals S.A., Lugano-Besso (CH)

( * ) Notice: Subject to any disclaimer, the term of this patent is extended or adjusted under 35 U.S.C. 154(b) by 0 days.

(21) Appl. No.: 10/312,520

(22) PCT Filed: Jun. 12, 2001

(86) PCT No.: PCT/EP01/06622

§ 371 (c)(1), (2), (4) Date: Jul. 3, 2003

(87) PCT Pub. No.: WO02/02219

PCT Pub. Date: Jan. 10, 2002

(65) Prior Publication Data

US 2004/0254402 A1 Dec. 16, 2004

(30) Foreign Application Priority Data

Jun. 30, 2000 (EP) .................................. 00113909

(51) Int. Cl.
*C07C 45/29* (2006.01)

(52) U.S. Cl. ....................................... 568/472; 568/493

(58) Field of Classification Search ................ 568/472, 568/493

See application file for complete search history.

(56) References Cited

U.S. PATENT DOCUMENTS

| | | | | |
|---|---|---|---|---|
| 2,462,413 | A | * 2/1949 | Meath | ........................ 568/473 |
| 2,504,402 | A | 4/1950 | Field | |
| 2,519,788 | A | * 8/1950 | Payne | ........................ 260/603 |
| 4,358,623 | A | 11/1982 | Murphy et al. | |
| 4,450,301 | A | 5/1984 | McMillan et al. | |
| 5,997,826 | A | 12/1999 | Lodeng et al. | |
| 6,147,263 | A | * 11/2000 | Wachs et al. | ................ 568/473 |

FOREIGN PATENT DOCUMENTS

GB 1 463 174 A 2/1977

* cited by examiner

*Primary Examiner*—Sikarl A. Witherspoon
(74) *Attorney, Agent, or Firm*—Akerman Senterfitt

(57) ABSTRACT

A method for formaldehyde production through catalytic oxidation of methanol, comprising the steps of feeding to a first oxidation catalytic bed (2) a gas flow comprising methanol and oxygen at a predetermined crossing linear flow rate, obtaining at the outlet of said first catalytic bed (2) a flow of gaseous reaction products comprising unreacted methanol, and feeding the flow of gaseous products to a second oxidation catalytic bed (6) is distinguished by the fact that the flow of gaseous reaction products comprising unreacted methanol is fed to the second catalytic bed (6) with a crossing linear flow rate substantially equal to said predetermined first catalytic bed (2) feeding flow rate.

3 Claims, 5 Drawing Sheets

METHOD FOR THE PRODUCTION OF FORMALDEHYDE

DESCRIPTION

In its general aspect the present invention relates to a method for the production on an industrial scale of formaldehyde.

Specifically, the invention relates a method of the above-mentioned kind for formaldehyde production through catalytic oxidation of methanol.

More in particular, such method for the production of formaldehyde through catalytic oxidation of methanol comprises two steps.

The first step concerns the feeding to a first oxidation catalytic bed of a gas flow comprising methanol and oxygen at a predetermined feeding flow rate.

Following said oxidation, a flow of gaseous reaction products is obtained at the outlet of the first catalytic bed also comprising unreacted methanol.

The second step concerns the feeding of the flow of gaseous products to a second oxidation catalytic bed.

PRIOR ART

It is well known that the methanol oxidation reaction to formaldehyde is carried out feeding at a predetermined flow rate a flow of gaseous reactants comprising oxygen and methanol in a catalytic bed.

Such predetermined flow rate allows obtaining the partial conversion of the reactants into products, according to the residence times, the temperature and the nature of the catalyst of the catalytic bed.

It shall be considered that the methanol reaction into formaldehyde is exothermic, hence heat is released as the reaction proceeds.

As the reaction is catalytic, the same is carried out in the aforesaid catalytic bed, said bed being of the pseudo-isothermal type.

The expression "pseudo-isothermal catalytic bed" is meant to indicate a catalytic bed wherein the temperature is maintained within a relatively narrow range of values by means of heat removal through a heat exchange surface.

Such catalytic bed is made of tubes inside which the catalyst is introduced, such tubes being arranged parallel to each other and building up a tube bundle.

The tubes filled with catalyst are crossed by the gaseous reactants and externally are lapped by a fluid intended for the continuous heat removal, which is not anyway large enough for an effective reaction in isothermal conditions to take place.

Beside the continuous heat removal, it is in fact thanks to the suitable predetermined linear flow rate of such reactants in the tubes that it is possible to carry out said reaction in pseudo-isothermal conditions, trying to prevent the uncontrolled formation of carbon oxides and other by-products which are detrimental to formaldehyde.

For such reason, the gaseous reactants are made flow in such tube: bundle at a predetermined crossing linear flow rate, according to the required residence time.

The expression "residence time" is meant to indicate the minimum time required by the gas flow for crossing the catalytic bed, which is necessary for obtaining the desired reaction conversion yield. The term "crossing linear flow rate" is meant to indicate the flow rate of the reactants measured along a single crossing direction with respect to the catalytic bed, with reference to well defined gas temperature and pressure conditions.

A drawback that is initially encountered when carrying out such oxidation, is the presence in the gaseous reaction products of unreacted methanol, specifically undesired for some applications of the formaldehyde.

In order to reduce the amount of such unreacted methanol, the British Patent UK 1 463 174 proposed to carry out a second catalytic oxidation step of the methanol itself.

For such an additional oxidation, downstream of the first bed, a second catalytic bed is used to which the gaseous reaction products are fed at a reduced flow rate (0.5–0.25 times) with respect to the first catalytic bed feeding flow rate.

Such flow rate reduction is obtained through a larger transverse section of the second bed with respect to the first catalytic bed.

Further on, in such second bed no heat removal takes place, so that this operates in an adiabatic way.

As heat is not removed, the additional heat produced by virtue of this second oxidation causes an additional increase of temperature in such bed, increase which needs to be maintained within narrow limits in order not to damage the catalyst itself, making it possible to follow such modus operandi only in presence of low concentration of methanol.

In fact, the expression "hot spots" is used to indicate the phenomenon of inhomogeneous temperature increase involve first catalytic bed concerning only limited portions of the catalytic bed.

The larger amplitude of the section causes a decrease of the crossing linear flow rate between the first and the second bed, which increases the residence time of the products inside the catalytic bed.

This is disadvantageous for the purposes of the temperature control, of the completion of the reaction and of the catalyst life.

Sometimes, further on, the gas exiting from the reactor tubes in which the first oxidation occurs has substantial non homogeneity regarding flow rate and temperature from area to area, causing in the second bed phenomena of localized "hot spots".

Therefore, as with the aforesaid modus operandi it is not possible to control in a critical way the temperature inside the second catalytic bed, it is impossible to remove the rest from the final products. Such so structured second catalytic bed is hence little effective in completely converting the methanol into formaldehyde.

SUMMARY OF THE INVENTION

The technical problem underlying the present invention is that of providing a method for the production of formaldehyde from methanol with a high conversion degree, overcoming the drawbacks mentioned with reference to the prior art.

According to the invention, this problem is solved by a method comprising the steps of:
  feeding to a first oxidation catalytic bed a gas flow comprising methanol and oxygen at a predetermined crossing linear flow rate, obtaining at the outlet of the first catalytic bed a flow of gaseous reaction products comprising unreacted methanol;
  feeding the flow of gaseous products to a second oxidation catalytic bed;
  characterized in that:
  the flow of gaseous reaction products comprising unreacted methanol is fed to the second catalytic bed with a crossing linear flow rate substantially equal to the predetermined first catalytic bed feeding flow rate.

In case the methanol concentration is relatively high, with a corresponding intense heat production, it is foreseen to use a heat exchanger arranged between the two catalytic beds, that guarantees an adequate temperature control of the gas fed to the second bed.

The invention relates also to an apparatus aimed to complete the reaction, which has the features of claims 5–8.

BRIEF DESCRIPTION OF THE DRAWINGS

The present invention will be further described with reference to the attached drawings provided as an indicative and not limiting example only, in which.

DETAILED DESCRIPTION OF THE INVENTION

Figure 1:
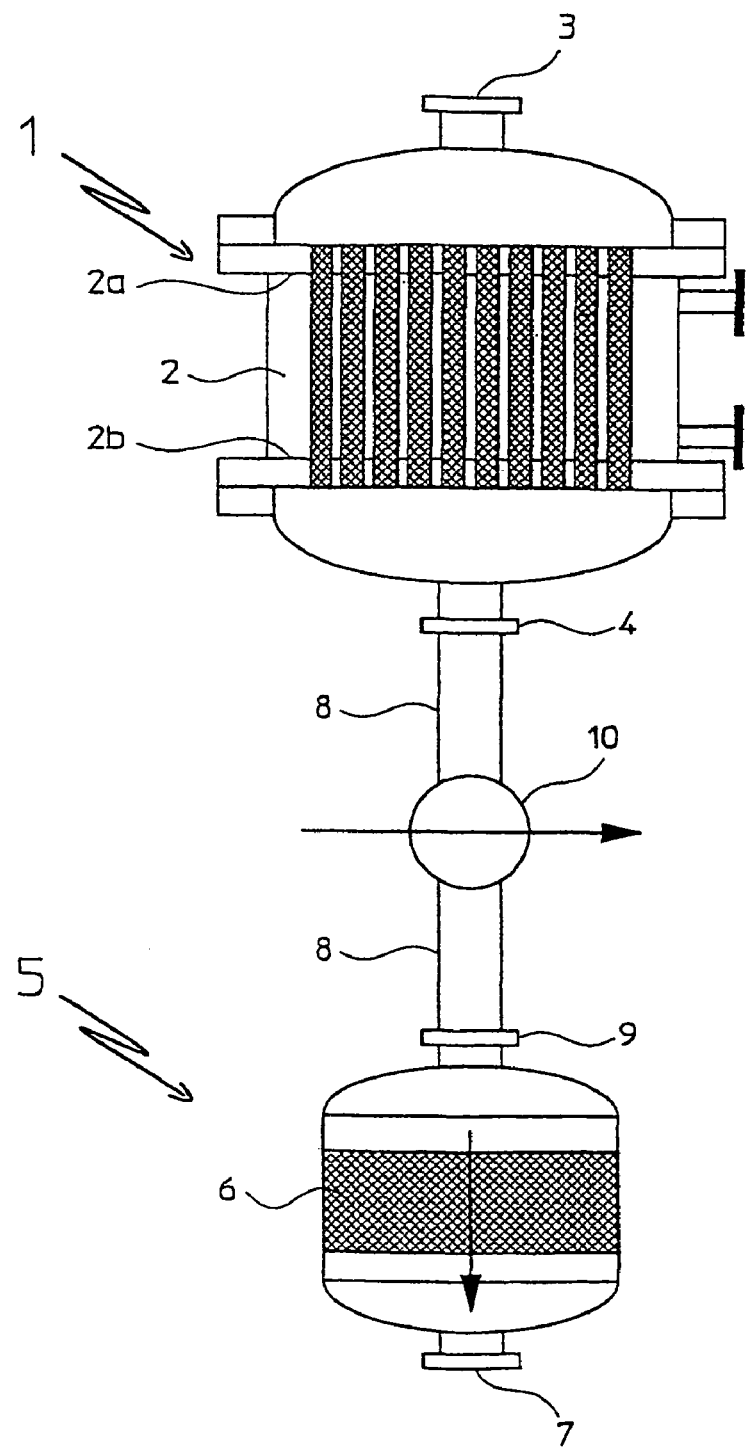
FIG. 1 shows schematically an apparatus for carrying out the method according to the present invention

With reference to FIG. 1, an apparatus for carrying out a method according to the present invention is shown in which a flow of gaseous reactants comprising methanol and oxygen is introduced in a first reactor 1 through an opening 3.

Such reactor 1, of substantially cylindrical shape, is of the type with inside it a pseudo-isothermal catalytic bed 2 consisting of a plurality of tubes filled with a Fe—Mo catalyst and forming in turn a tube bundle.

The inlet side of such catalytic bed is indicated with 2a and the outlet side with 2b.

Such catalytic bed 2 is characterized by a crossing transverse section of predetermined amplitude, such amplitude being so determined so as to obtain the suitable crossing linear flow rate for realising the conversion of methanol into formaldehyde.

As used herein, the expression "crossing transverse section" means the internal section of a duct or a catalytic bed, respectively.

Such section is measured perpendicularly to the flow direction inside the duct or the catalytic bed, respectively.

The reactor 1 is further equipped with an opening 4 to which a duct 8 is connected, that, according to the embodiment shown, leads to a heat exchanger 10.

Such duct 8 is connected, through the respective ends, to the reactor 1 through the opening 4 and to a reactor 5 through the opening 9.

The duct 8 is characterized by a crossing transverse section of predetermined amplitude.

Such duct has at least a portion with a transverse section characterized by a reduced amplitude with respect to the transverse section of the catalytic bed 2.

The reactor 5, of cylindrical shape, is provided at its ends with an opening 9 and an opening 7, respectively.

Inside said reactor 5, a cylindrical catalytic bed 6 of the adiabatic type is foreseen.

Such catalytic bed 6 is characterized by a crossing transverse section of predetermined amplitude, such amplitude being reduced with respect to the amplitude of the crossing transverse section of the first catalytic bed 2.

The flow of gaseous reactants is fed into the reactor 1 through the opening 3 at a temperature of 180° C.–200° C. and at a predetermined flow rate such that the crossing linear flow rate inside the catalytic tubes, calculated with reference to the temperature of 0° C. and at the atmospheric pressure, is in the order of 1.2–1.6 m/s.

Such predetermined flow rate guarantees an ongoing reaction, allowing at the same time a satisfying control of the oxidation temperature.

Such flow is in fact submitted to catalytic oxidation in bed 2, whereas the reaction heat is transferred to a suitable diathermic fluid circulating outside of the catalytic tubes.

Through such cooling technique, the gas flow is maintained within a temperature range, which, however, at the location where the heating of the bed is the greatest, will reach 380–420° C.

As used herein, the term "diathermic fluid" means a fluid for the heat exchange at high temperatures that in those conditions may even be subject to changes in its physical state.

The gaseous reaction products exit from the outlet side 2b of the catalytic bed 2.

Immediately downstream of the outlet of the tubes, the section of the reactor 1 substantially increases, with ensuing drastic reduction of the crossing linear flow rate of the gas.

Such cooled products still comprise unreacted methanol; this is the reason why they are fed into a second catalytic bed 6 and further reacted by means of an additional oxidation, as will be clear from the following description.

In order to control in a critical way said methanol removal, avoiding undesired temperature peaks, according to the present invention, said gaseous reaction products, according to this embodiment of the present invention here shown, are suitably cooled down before being fed to the catalytic bed 6.

Such further cooling occurs at the outlet of the reactor 1 by means of the heat exchanger 10 and cool the gaseous products to a temperature comprised between 200 and 300° C.

Such cooling shown in this embodiment of the invention is anyway necessary only in case the percentage of unreacted methanol present in the gaseous products at the outlet of the catalytic bed 2, is greater than a value equal to some percentage points of its inlet concentration to the reactor 1.

The gaseous reaction products partially converted in the catalytic bed 2 and cooled after having crossed the heat exchanger 10 are fed, through the duct 8, in a second reactor 5 comprising a second catalytic bed 6 wherein the reaction is completed through a second catalytic oxidation that transforms the unreacted methanol into formaldehyde.

The reaction gaseous products cross the bed 6 in a direction parallel (axial flow) to its main axis.

In the present embodiment of the invention, the aforesaid amplitude of the crossing transverse section of the catalytic bed 6, is reduced with respect to that one arranged immediately downstream of the bed 2 so to guarantee a crossing linear flow rate of the gaseous products inside the bed 6, substantially similar to the one inside the catalytic bed 2.

The reaction gaseous products, once the unreacted methanol has been transformed into formaldehyde, are discharged through the opening 7 of the second reactor 5, products that comprise formaldehyde and are practically methanol-free.

As mentioned above, in case the methanol percentage contained in the flow of gaseous products entering into said bed is very limited, the reaction can reach its completion in the catalytic bed 6, without the exchanger 10 being used.

In the aforesaid case, the temperature of the gaseous products as a consequence of the oxidation in the second bed 6 does not reach high values because, as it is low the amount of methanol which reacts, it is also small the amount of heat produced and hence the increase of temperature is kept within acceptable limits without external intervention.

In this instance, the reaction gaseous products, in a not shown embodiment of the invention, once crossed the catalytic bed 2, are fed through the duct 8 directly into the catalytic bed 6, wherein the reaction will be terminated without the heat exchanger 10 being used.

Should the methanol be present in significant although limited concentrations and not only in traces, it will be possible to avoid the use of the exchanger 10 as the crossing linear flow rate of the products inside the catalytic bed 6 is substantially similar to that one inside the catalytic bed 2 and guarantees the necessary control on the distribution of temperature.

Such flow rate value is obtained through the specific sizing of the crossing transverse section of the bed 6, that has a reduced amplitude with respect to that arranged immediately downstream of said bed 2.

Such reduced amplitude of the section causes an increase of the flow rate, guaranteeing the achievement of the condition required inside the catalytic bed 6 for a correct completion of the oxidation reaction.

Therefore, it is convenient realising the new catalytic beds of the adiabatic type so that they are characterized by a greater crossing flow rate with respect to those of the prior art, thus distributing the thermal load which is sometimes localized as a "hot spot" to which the catalyst is subject, that can reduce its effectiveness with time.

The residence time and the crossing linear flow rate are in fact controlled according to the kinetics itself of the reaction, to the gaseous products flow rate and to the transverse section of the catalytic bed.

Anyway, the amount of the energy consumption needed for obtaining the required flow rate shall be evaluated; such energy is needed to compensate for the pressure drops caused during the crossing of the catalytic bed 6, and it can be found not convenient to work at too high flow rates from an energy balance point of view.

In view of the aforesaid reasons, it is particularly advantageous in the present invention to achieve adequate flow rates, which are useful both for enhancing the reaction yield and for obtaining a limited consumption of energy and a longer catalyst service life.

Figure 2:
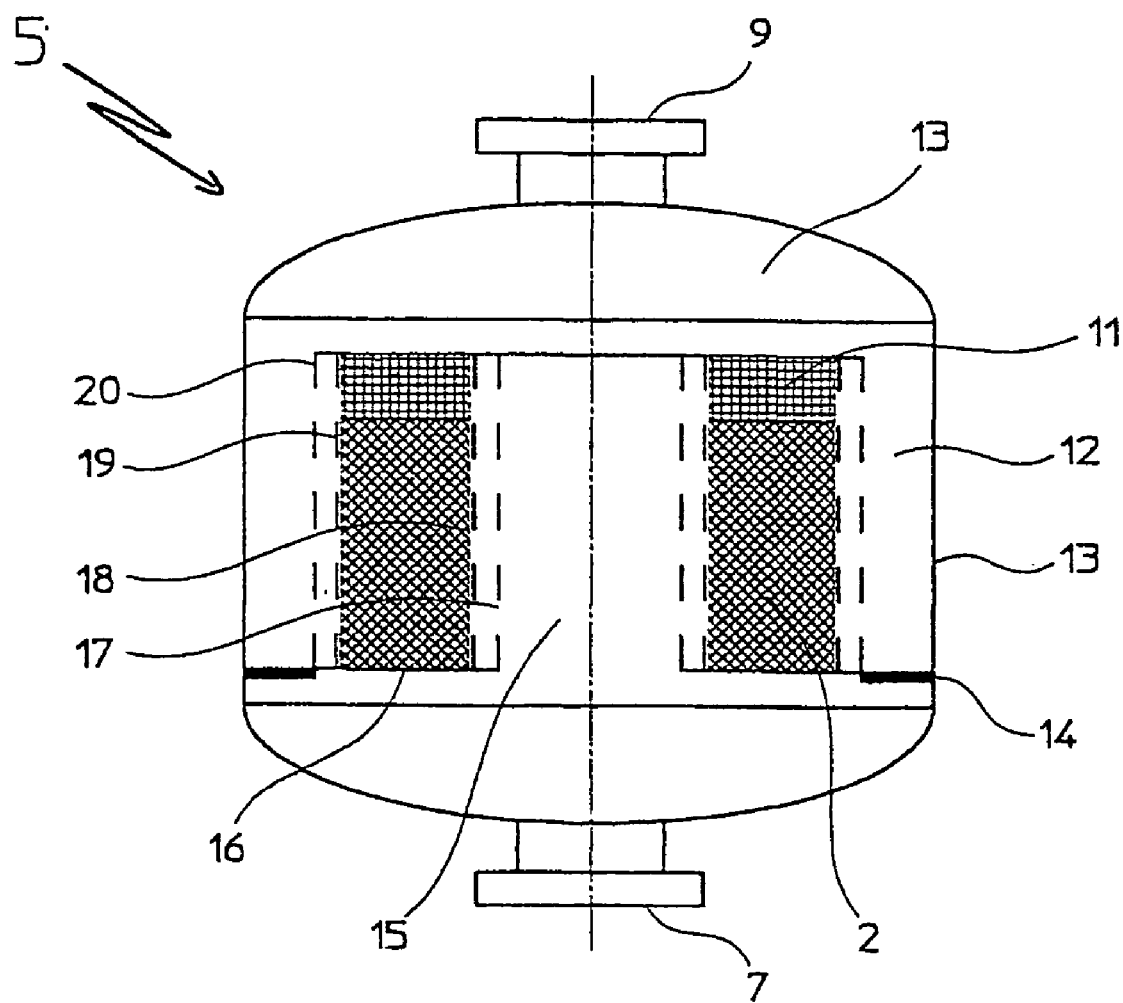
FIG. 2 shows schematically a reactor according to an alternative embodiment of the apparatus of FIG. 1.

With reference to FIG. 2 there is shown an alternative embodiment of the invention, wherein reactor 5, in which the second oxidation takes place, comprises a catalytic bed 2 crossed by gaseous reaction products in a direction perpendicular to its axis (radial flow instead of axial flow).

Such embodiment advantageously implies at equal yield a decrease of operating costs, because of the lower pressure drops obtained by such alternative embodiment as reported hereinbelow.

Such cylindrically shaped bed 2 is characterized by a reduced thickness of the catalytic layer with respect to analogous kinds of axial catalytic beds.

The reduced thickness of the bed 2 favours the crossing by the reaction gaseous products, reducing the energy consumption.

Such catalytic bed 2 is so structured so as to define a cylindrical inner chamber 34.

An annular gap 12 separates the outer sidewall 13 of the bed 2 from the gas-permeable wall 20, which is inside the reactor 5.

The openings 9 and 7 guarantee the inlet and outlet of the gaseous products that cross the reactor 5, respectively.

The catalytic layer forming the catalytic bed 2 is delimited sideways by gas-permeable walls 18 and 19, in its upper part by the layer 11 formed by granular material that does not take part to the reaction and in its lower part by the bed bottom 16, such bottom being impermeable to gases.

The bed 2 is inserted in a cage structure externally delimited by the aforesaid wall 20 and internally by the wall 17, which is also perforated; the whole assembly is supported by means of said bottom 16 on means 14 arranged on the inner side of the reactor.

The reaction gaseous products coming from the first reactor 1, with reference to FIG. 2, containing oxygen, methanol and formaldehyde flow through the aforesaid inlet opening 9 into an area 13 aimed at distributing the gases in the reactor so that they are conveyed inside the annular gap 12.

From such annular gap, the gaseous reaction products reach with a radial flow pattern, the catalytic bed 2 through the gas-permeable wall 20 and the cylindrical gap provided between the permeable walls 20 and 19.

The transformed and methanol-free gaseous products reach the cylindrical chamber 15 through the permeable walls 17 and 18 and finally leave the reactor through the opening 7.

Once they leave the reactor, these products are substantially free of unreacted gaseous methanol.

Figure 5:
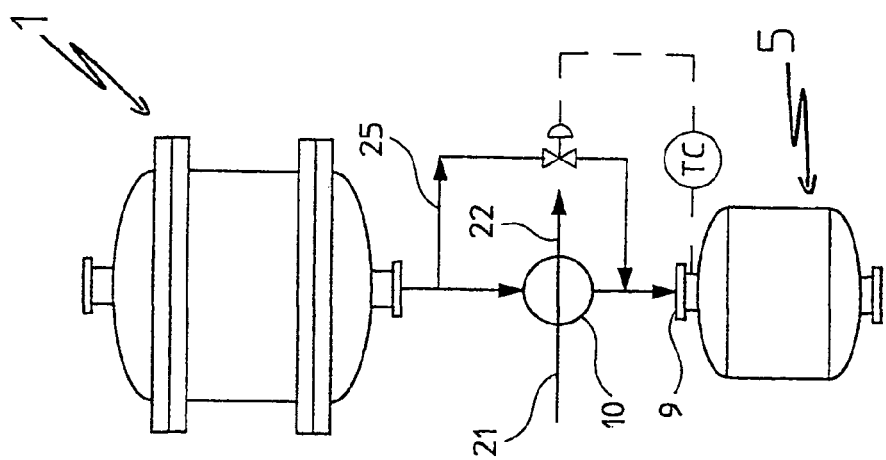
FIGS. 3 to 5 show further alternative embodiments of the apparatus according to the invention.
Figure 4:
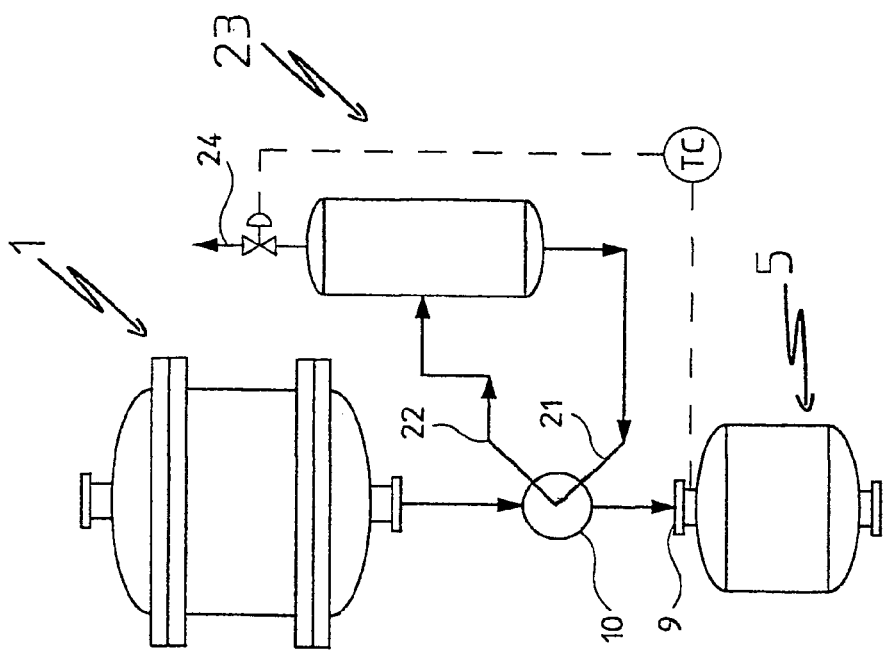
Figure 3:
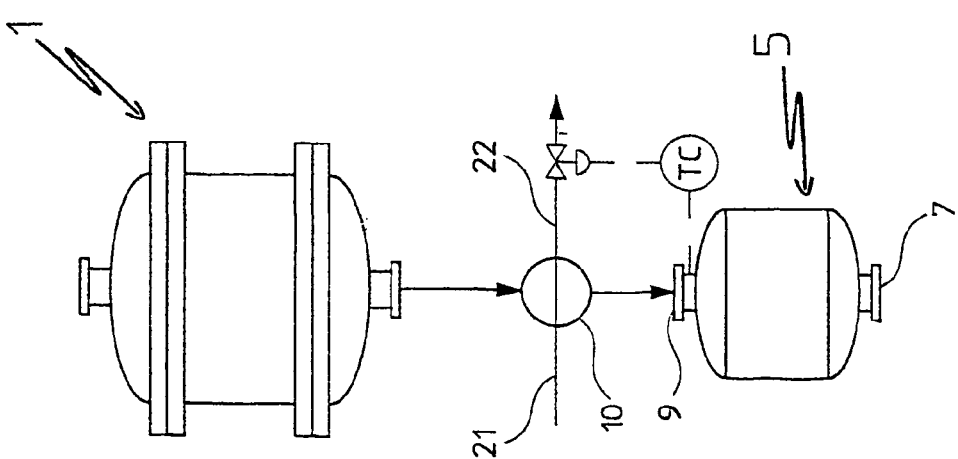

In order to guarantee an effective control of the inlet temperature of the gas into the second catalytic bed when the apparatus is operating, arrangements with reference to FIGS. 3, 4 and 5 may be used.

Thus, for example with reference to FIG. 3, the control is accomplished through a device which, by measuring the temperature of the gaseous products at the inlet 9 of reactor 5, operates adjusting the flow of a coolant that flows across the heat exchanger 10 through the pipelines 21 and 22.

With reference to FIG. 4, the temperature control is carried out by means of a device that measures the temperature in the opening 9 for the gas inlet of the reactor 5, controlling the steam pressure of a boiler 23 used for heat recovery.

Such boiler uses the heat released inside the exchanger 10 by the reaction gaseous products in order to produce steam at a temperature determined by the control of the boiler pressure.

The control device operates directly adjusting the pressure of boiler 23 by throttling line 24.

Finally, with reference to FIG. 5, the temperature control is accomplished by means of a device according to which a first portion of the gaseous products to be cooled coming from the reactor 1 crosses the exchanger 10 and a second portion is made to flow externally of the exchanger 10 inside the duct 25 in order to be fed directly inside the reactor 5, in an amount determined by the device for the temperature control.

The device operates just on such flow portion in order to carry out the temperature control.

Figure 6:
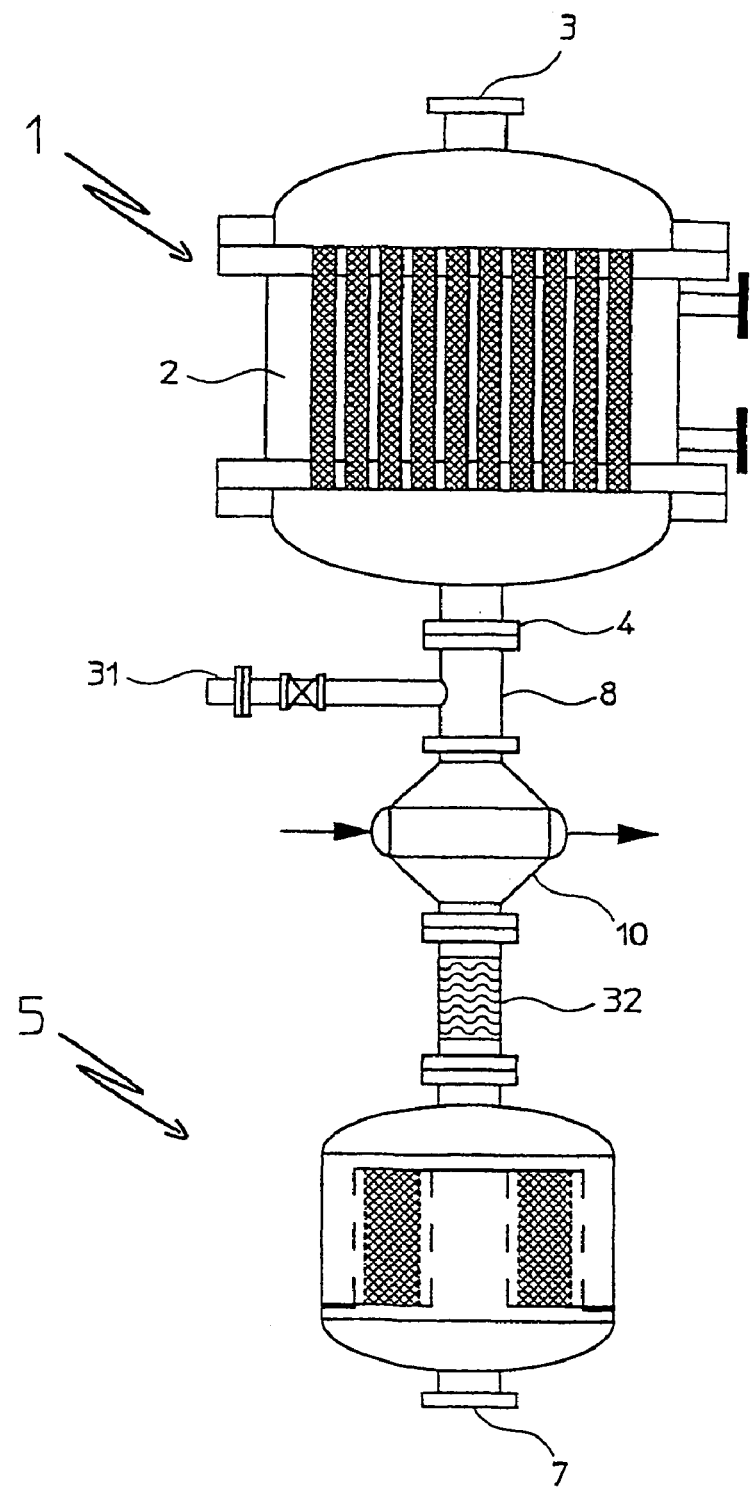
FIG. 6 schematically shows a reactor according to an alternative embodiment.

The invention so conceived may be modified or changed with all the alternative embodiments falling within the same inventive concept; thus, for example and with reference to FIG. 6, a reactor according to the invention is shown equipped with a duct 31 for feeding an additional flow of gas containing oxygen.

The requirement to provide an alternative embodiment with such an arrangement, is due to the necessity to guarantee the reaction of methanol and oxygen with an amount of oxygen adequate both for the reaction stoichiometry and the maintenance of the oxidation state required by the catalyst particles.

Differently from the previous ones, the apparatus obtained according to this embodiment has an additional duct 31 that is inserted inside the duct 8, such duct connecting the outlet opening 4 of the reactor 1 and the exchanger 10.

Through such duct 31 a flow of gas containing oxygen is added to the flow of gaseous products coming out from the opening 4 of the first reactor 1.

In order to achieve an optimum mixing between the additional flow of oxygen and that one coming out from the first reactor, a mixer 32 is foreseen downstream of the exchanger 10 which operates effectively once the gaseous products have already been cooled.

It shall be considered that such alternative embodiment, beside carrying out an effective control of the oxidation state of the catalysts, important for their activity, and guaranteeing a feed of oxygen to the methanol oxidation reaction, allows carrying out a preliminary cooling of the gaseous products coming out from the reactor 1.

Figure 7:
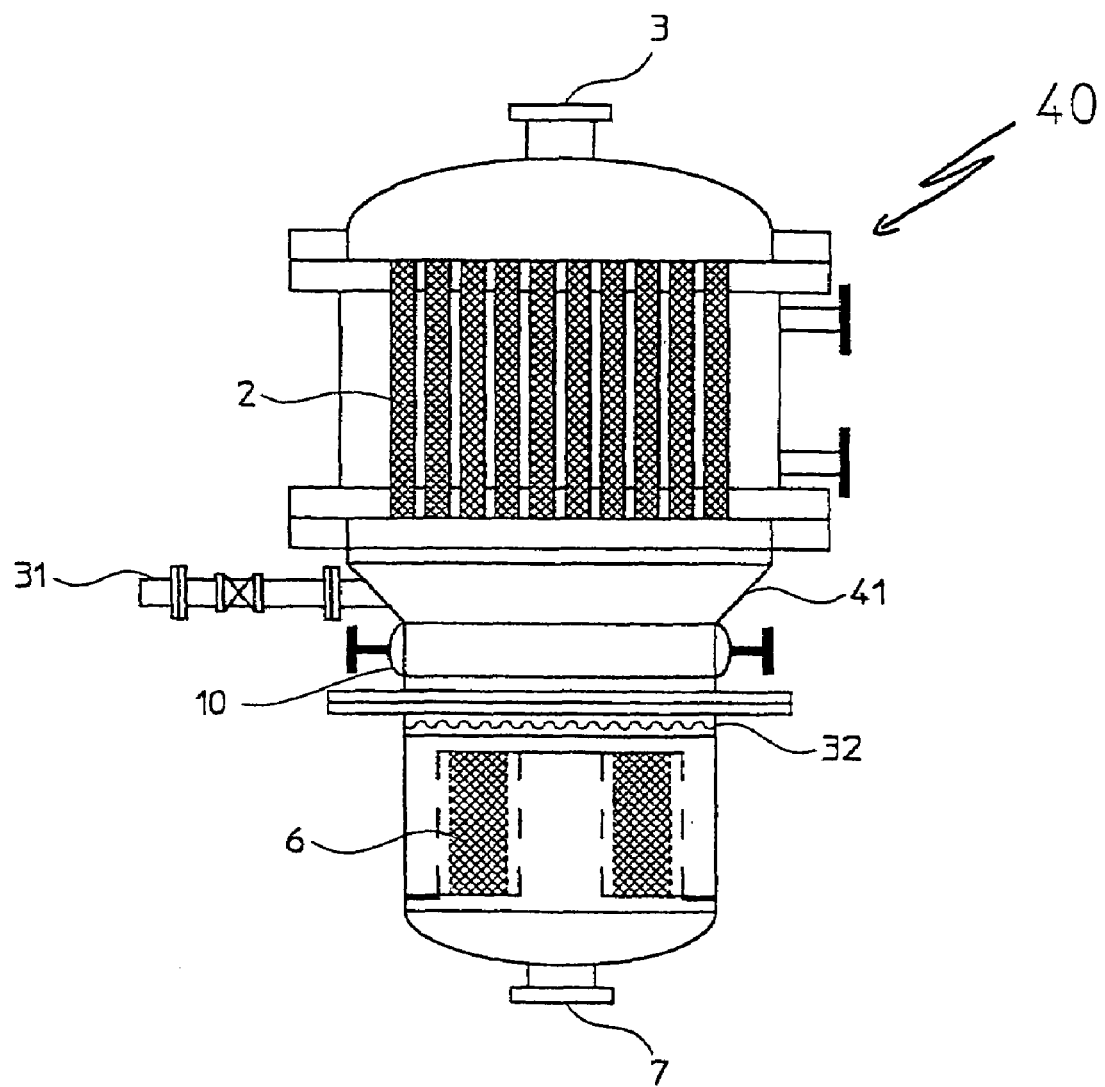
FIG. 7 schematically shows a reactor according to a further alternative embodiment.

With reference to FIG. 7, an embodiment of the invention is shown which is alternative to that one of FIG. 6, carried out in a single reactor 40 equipped with a first catalytic bed 2 and a second catalytic bed 6, in fluid communication through an amplitude reducer 41 of the crossing transverse section. Reducer 41 is equivalent and has the same function of duct 8 shown in the previous figures.

A duct 31 for feeding an additional flow of gas containing oxygen is connected to such reducer 41.

In such embodiment, a heat exchanger 10 and a mixer 32 are foreseen, which are both arranged in such single reactor 40.

Finally, in such reactor 40 a catalytic bed 6 of reduced crossing transverse section with respect to the section immediately downstream of the catalytic bed 2 is foreseen.

Such bed 6 is of the type shown with reference to FIG. 2.

The feeding of such reactor 40 occurs in the same way disclosed in the previous embodiments of the reactor.

The advantage achieved with such embodiment is that of obtaining a reduced overall size for the apparatus.

Some non-limiting examples of implementation of the method of the present invention are listed hereinbelow.

REFERENCE EXAMPLES

Example 1

A reactor according to the prior art is formed by 6000 catalytic tubes having a 20 mm inner diameter, a 800 mm high catalytic bed, comprising an upper layer of catalytic particles being arranged on a layer of catalytic rings placed underneath.

The reactor is fed with 8500 $Nm^3/h$ of gas thus reaching a flow rate equal to 1.25 Nm/s.

Such gas contains 7% in volume of methanol and 10% in volume of oxygen. The inlet temperature is 200° C. and the diathermic fluid that laps the tubes externally is maintained at a temperature of 270° C.

The better yield achieved is 92.3% of reacted methanol in formaldehyde, whereas the methanol concentration in the gas leaving the reactor is 0.25%.

The gas then absorbed in water in order to obtain 1840 kg/h of a 40% formaldehyde solution contains 1.5–1.6% of unconverted methanol.

The same reactor is equipped with a second catalytic bed of the adiabatic type formed by an additional catalytic layer formed by the same type of ring-like catalyst introduced in the catalytic tubes located above it.

The overall bed volume is 360 liters with a thickness of 70–80 mm. The operative conditions are similar to those already described for the first reactor.

The crossing linear flow rate of this bed is equal to 0.5 m/s, thus 40% of the crossing flow rate of the pseudo-isothermal bed that comes before it.

The reaction gaseous products coming out of the tubes have a temperature of 293° C., and reach temperatures in the range 296° C. to 305° C. by crossing the adiabatic catalytic bed.

The methanol concentration in the gas discharged from the reactor is 0.16% and the formaldehyde solution obtained contains 1.1% in weight of unconverted methanol.

The reduced concentration of methanol inside the formaldehyde solution obtained with the addition of the catalyst adiabatic layer without varying the operative conditions, exhibits the advantages relative to the addition of an additional catalytic layer, although only a small increase in the amount of reacted methanol is obtained.

When the methanol concentration in the feed gas increases from 7 to 8% in volume, the practical limit is given by the temperature peaks inside the tubes of the tubular reactor. The methanol content in the reacted gases coming out of the catalytic bed reaches a value higher than 0.56%, more than the double of the previous case. The adiabatic catalytic bed is capable of reducing such amount to a value below 0.27%. Although the methanol fed is increased by 14.3%, by virtue of a lower reaction selectivity the production increase in the 40% formaldehyde solution is just 11–12% and the content of residual methanol is 1.6% in weight.

The temperature increase inside the adiabatic bed is 40–25° C., and is not homogeneously distributed along the bed where hot spots are to be found that reach even 400° C. Such spots are risky for the possibility of altering the oxidation process causing serious damages to the catalyst activity.

Example 2

A first reactor of the pseudo-isothermal type was used without varying the operating conditions of example 1. The gas coming from the primary reactor, available at a temperature of 305° C., is cooled according to the invention to 260° C. before being introduced into a secondary reactor of adiabatic type. The cooling is obtained in a boiler that produces saturated vapor at 12 bar.

The adiabatic catalytic bed has a 1500 mm diameter, 320 mm thickness, in order to achieve the preferred crossing linear flow rate of the invention, equal to 1.35 Nm/s.

After having crossed the catalytic bed, an evenly distributed temperature increase is encountered corresponding to a final temperature of 290–310° C., hence free of too inhomogeneous values. The pressure drop for the crossing of the second reactor is 0.08 bar.

The concentration of reacted methanol in the treated gas is 0.16% in volume that takes the total level of reacted methanol to 98.7%.

In the preferred embodiment of the invention shown in FIG. 2, the secondary reactor is designed in such a way that the gas crosses it in radial direction.

The basket contains 660 kg of catalyst of the same type as for example 1. The catalytic bed having a respective outer and inner diameter equal to 1200 and 600 mm, respectively, is defined between two cylindrical vertical walls made of stainless steel with a mesh coating 8.

The bed is hold by a horizontal bottom plate of the basket made of a stainless steel sheet. The process gas is introduced into the secondary reactor through the upper opening, in order to be distributed around the perforated cylindrical surface externally to the mesh coating containing the catalyst and forming with said coating a closed distribution chamber, with a width of 10 mm.

After having crossed the catalytic bed in radial direction towards the inside, the gas reaches the collection chamber defined by said coating and by a further perforated wall, arriving into the central chamber of the basket, from which it is discharged through an opening on the bottom.

The temperature increases by about 45° C. distributed inside the inner surface of the basket in a range from 3 to 4° C. and measures 305° C. at the outlet.

The methanol concentration is negligible thus demonstrating its complete conversion.

The invention claimed is:

1. A method for the production of formaldehyde through catalytic oxidation of methanol, comprising the steps of:

feeding to a first oxidation catalytic bed a gas flow comprising methanol and oxygen at a predetermined crossing linear flow velocity, obtaining at the outlet of said first catalytic bed a flow of gaseous reaction products comprising unreacted methanol; and feeding said flow of gaseous products to a second oxidation catalytic bed;

wherein said flow of gaseous reaction products comprising unreacted methanol is fed to said second catalytic bed with a crossing linear flow velocity substantially equal to said predetermined first catalytic bed feeding flow velocity.

2. The method according to claim 1, wherein said gaseous reaction products fed to said second catalytic bed have a temperature that is controlled in a temperature range comprised between 200 and 300 C.

3. The method according to claim 2, wherein said temperature range is comprised between 210 and 260 C.

* * * * *